United States Patent [19]

Lenmark, Sr. et al.

[11] Patent Number: 4,997,090
[45] Date of Patent: Mar. 5, 1991

[54] BIOLOGICAL SAMPLE VIAL TRANSPORT TRAY

[75] Inventors: Voigt O. Lenmark, Sr., St. Louis Park; William A. Koentopp, St. Paul, both of Minn.

[73] Assignee: Transpan Company, Minneapolis, Minn.

[21] Appl. No.: 534,444

[22] Filed: Jun. 7, 1990

[51] Int. Cl.⁵ .............................................. B65D 85/42
[52] U.S. Cl. ............................. 206/570.000; 206/443; 206/446; 220/94 A; 220/334
[58] Field of Search ............... 206/427, 443, 446, 564, 206/570, 139; 211/74, 76; 220/94 A, 94 R, 334

[56] References Cited

U.S. PATENT DOCUMENTS

| | | | |
|---|---|---|---|
| 2,430,222 | 11/1947 | Goldbert | 220/334 |
| 2,880,865 | 4/1959 | Knox | 206/564 |
| 3,643,812 | 2/1972 | Mander et al. | 206/564 |
| 4,319,683 | 3/1982 | Correa, III | 220/94 R |
| 4,434,890 | 3/1984 | Sieck et al. | 206/443 |
| 4,501,360 | 2/1985 | Levy et al. | 206/446 |
| 4,550,828 | 11/1985 | Baldwin et al. | 220/94 R |
| 4,720,021 | 1/1988 | Byrns | 220/94 R |
| 4,826,003 | 5/1989 | Levy | 206/443 |

FOREIGN PATENT DOCUMENTS

| | | | |
|---|---|---|---|
| 0678458 | 12/1964 | Italy | 220/334 |
| 0405352 | 2/1934 | United Kingdom | 220/94 R |

Primary Examiner—Jimmy G. Foster
Attorney, Agent, or Firm—Kinney & Lange

[57] ABSTRACT

A biological vial transport tray is provided comprising a hollow tray portion having a base, a plurality of side walls and a plurality of end walls. A center handle having a grip portion is provided. The center handle projects from the base. A pair of cover lids are also provided. Each cover lid is pivotally connected to the side walls of the tray portion by an arm extending from a pivot point in the end walls to a pivot point in the cover lid.

9 Claims, 4 Drawing Sheets

BIOLOGICAL SAMPLE VIAL TRANSPORT TRAY

BACKGROUND OF THE INVENTION

The present invention relates to trays for medical or laboratory use, and in particular, it relates to compartmented trays, each having a cover and a handle, for carrying vials for biological samples.

The use of trays for medical and laboratory use, for the purpose of carrying vials of such items as blood and urine, is well known. For instance, the Great Britain Patent No. 2,173,174 describes a package for vials comprising a block of shock absorbent material with a plurality of bores extending therethrough. A separate piece of shock absorbent material is placed at the bottom of the bores with a yet another separate piece of shock absorbent material placed across the bores. A sleeve holds the block and the absorbent material pieces in position.

SUMMARY OF THE INVENTION

A biological vial transport tray is provided comprising a hollow tray portion having a base and a plurality of side walls and a plurality of end walls. A center handle projects from the base. In a preferred embodiment, the tray portion and the center handle are molded from a single piece of material.

A pair of cover lids are also provided. Preferably, each cover lid is transparent. Each cover lid is pivotally connected to the end walls of the tray portion by an arm extending from a pivot point in the end walls to a pivot point in the cover lid. The cover lid preferably includes a handle.

In addition, the tray portion also includes a stop rod. The stop rod is positioned in the end walls such that an arm of an associated cover lid will rest against the stop rod when the cover lid is pivoted off the tray portion to open the cover.

A rectangular receptacle is positioned within the tray portion such that the receptacle rests upon the base and fits snugly between the side walls. The receptacle preferably includes a piece of shock absorbent material having at least one hole extending therethrough for holding a vial.

A plurality of fingers extend outward from one of the end walls. The fingers are adapted to securely hold a box of medical or laboratory gloves situated such that the medical or lab technician can easily access the gloves when the gloves are needed.

A pocket or pouch extends outward from at least one of the end walls. The pocket is adapted to hold a box of medical or laboratory gloves, or store documents associated with the medical or laboratory vials.

DETAILED DESCRIPTION OF THE PREFERRED EMBODIMENTS

Figure 1:
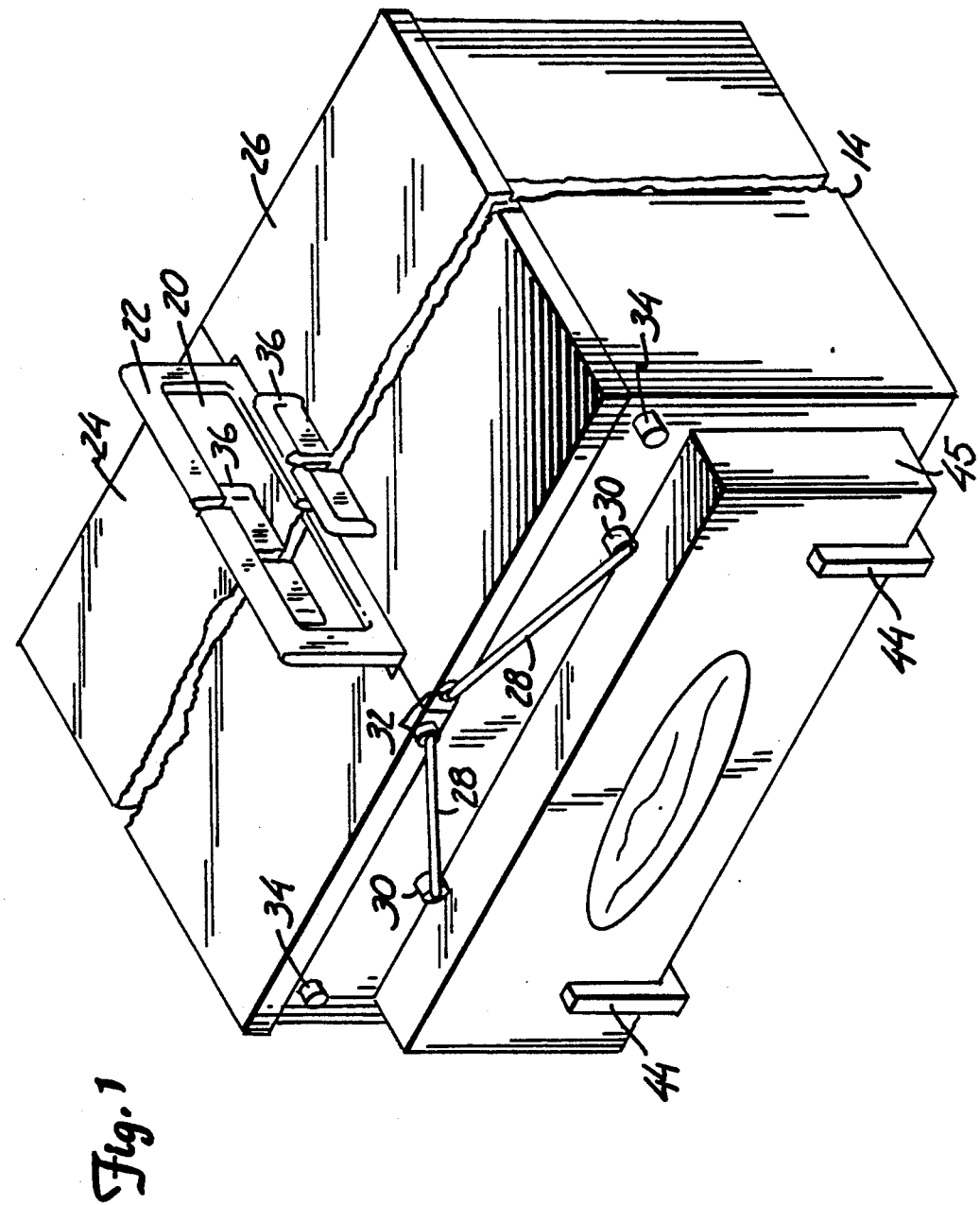
FIG. 1 is a perspective view of the biological sample vial transport tray of the present invention.
Figure 2:
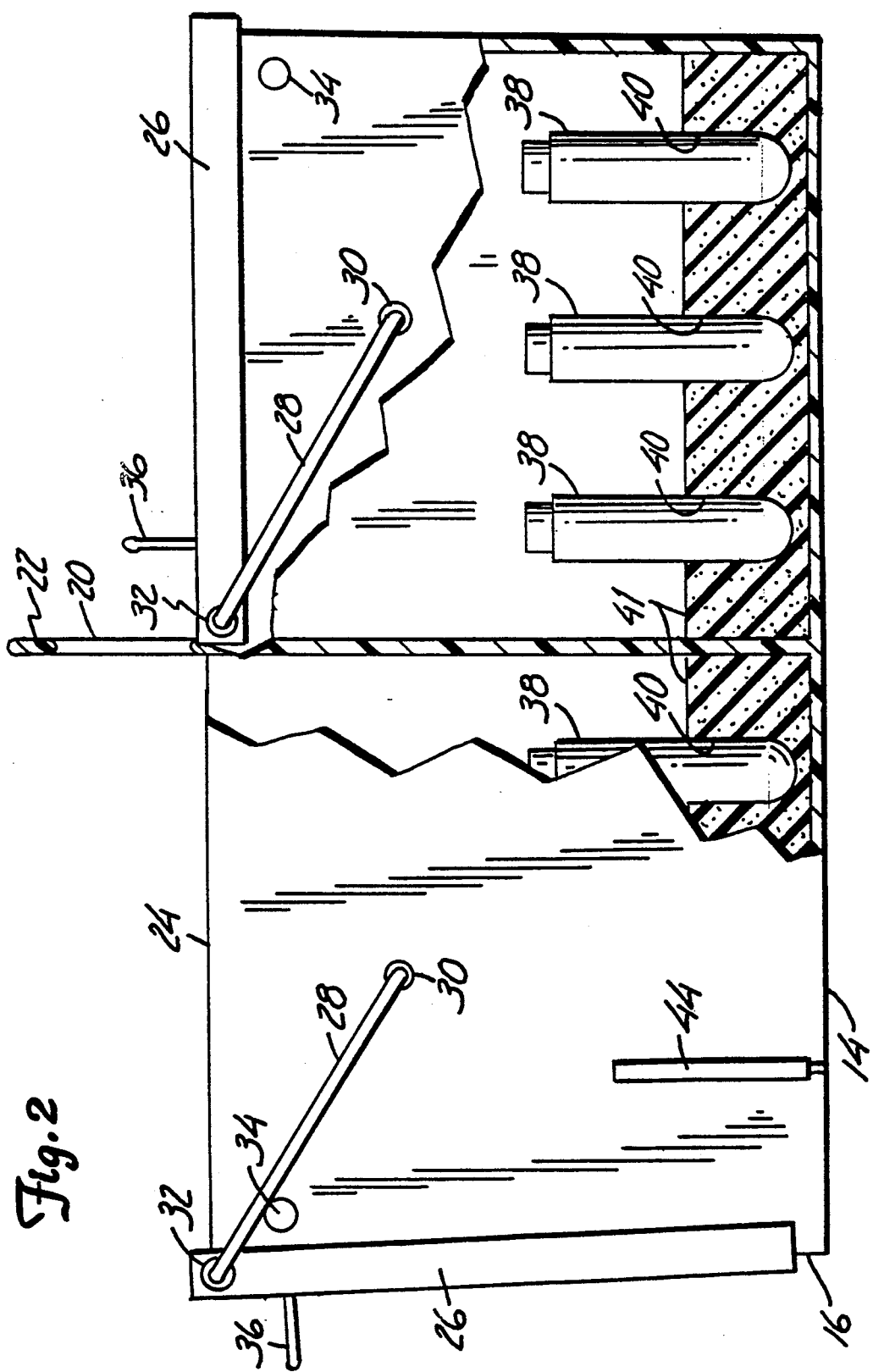
FIG. 2 is a side view of the biological sample vial transport tray of the present invention with one cover open and the other closed, and with parts broken away.
Figure 3:
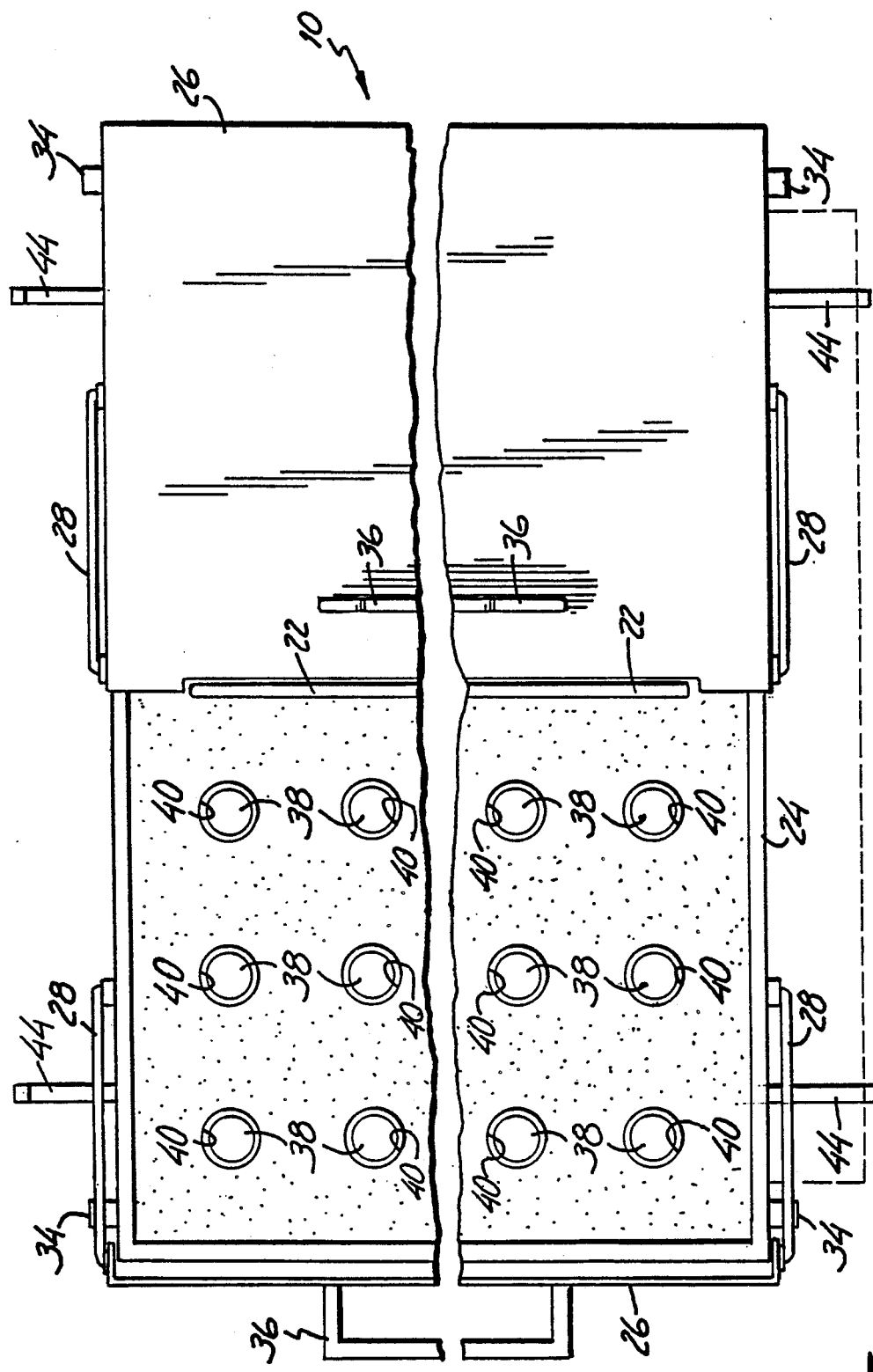
FIG. 3 is an top view of the biological sample vial transport tray of FIG. 1.

The biological vial transport tray of the present invention is generally indicated at 10 in FIGS. 1, 2 and 3. The tray 10 includes a hollow tray portion 12 having a base 14 and a plurality of side walls 16 and a plurality of end walls 17. The tray portion 12 is molded from a plastic material such that the side walls 16 and the end walls 17 are integral with the base 14 and integral with each other.

A center handle 20 projects from the base 14 and past the side walls 16 and the end walls 17 and has a grip portion 22. The grip portion 22 is preferably molded into the center handle 20. Preferably, the tray portion 12 and the center handle 20 are integrally molded.

The preferred embodiment of the tray 10 includes two parallel side walls 16 and two parallel end walls 17. Each side wall 16 is substantially perpendicular to each end wall 17. The side walls 16 and the end walls 17 are preferably substantially perpendicular to the base 14 and together the side walls 16 and the end walls 17 form a rim 24 around the tray portion 12. The integral connection between the side walls 16, the end walls 17 and the base 14 prevents any laboratory or medical samples, which could possibly spill or leak from the vials, from leaving the tray portion 12.

A pair of cover lids 26 having front edges 27, 29 are provided such that the cover lids 26 overlie the rim 24 of the side walls 16. Preferably, the cover lids 26 are formed from a transparent plastic such that a medical technician or laboratory assistant can view the vials through the cover lids 26 to determine whether any leakage or spillage had occurred before the cover lids 26 are opened. However, cover lids 26, which are translucent or opaque, are also within the scope of this invention.

The cover lids 26 are each connected to the tray portion 12 by a pair of arms 28 extending from a pivot point 30 in the end walls 17 of the tray portion 12 to a pivot point 32 in the respective cover lid 26. The arm 28 is in the form of a C-shaped metal rod and is connected to each pivot point 30, 32 in a known manner such that the arm 28 can freely pivot at each of the pivot points 30, 32.

The cover lids 26 pivotally travel to both a closed and open position as best illustrated in FIG. 2. When the cover lids 26 are pivotally moved to a closed position, the front edge 27 of one cover lid 26 encounters the front edge 29 of the other cover lid 26 and the center handle 20 to rest against the other cover lid 26 and the center handle 20 and substantially cover the tray portion 12. By having the front edges 27, 29 meet with each other, the medical or laboratory samples are hidden from view, when using translucent or opaque cover lids 26, thereby eliminating the unsightly nature associated with such samples.

The tray portion 12 preferably includes a stop rod 34 securely attached to the end walls 16. The stop rod 34 is positioned such that the arm 28 will rest against the stop rod 34 when the cover lid 26 pivotally travels off the tray portion 12. The stop rod 34 prevents the cover lids 26 from pivoting beyond a certain point and allows the cover lids 26 to rest against the side walls 16 when the cover lids 26 are in an open position as best illustrated in FIG. 2.

A pair of cover handles 36 can also be provided. Each cover handle 36 is secured to one of the cover lids 26.

The cover lids 26 and the cover handles 36 can be molded from a single piece of material. The material is can be of the same type as that which forms the tray portion 12 although different types of material may be utilized. It should be noted that the cover handles 36 could also be constructed of material different than that of the cover lids 26 and connected to the cover lids 26 in a known manner.

A rectangular resilient retainer pad 41 is positioned within the tray portion 12 such that the receptacle 41 rests upon the base 14 and fits snugly between the side walls 16 and the end walls 17. The pad 41 comprises a piece of shock absorbent material having at least one hole 40 (in practice, several are provided) extending therethrough for holding a standard medical or laboratory vial 38. The vials 38 are inserted in the holes 40 of the receptacle 41 and are frictionally held therein. Preferably, the vials 40 include a cap to prevent spillage of the vial contents.

In a preferred embodiment, best illustrated in FIGS. 1 and 3, a plurality of fingers 44 extend outward from at least one of the end walls 17 for securely holding a box 45 containing medical or laboratory gloves. The fingers 44 include an upward extending member 46 as illustrated in FIG. 1. The fingers 44 are adapted to securely hold a box 45 of medical or laboratory gloves situated such that the medical or lab technician can easily access the gloves when the gloves are needed.

Figure 4:
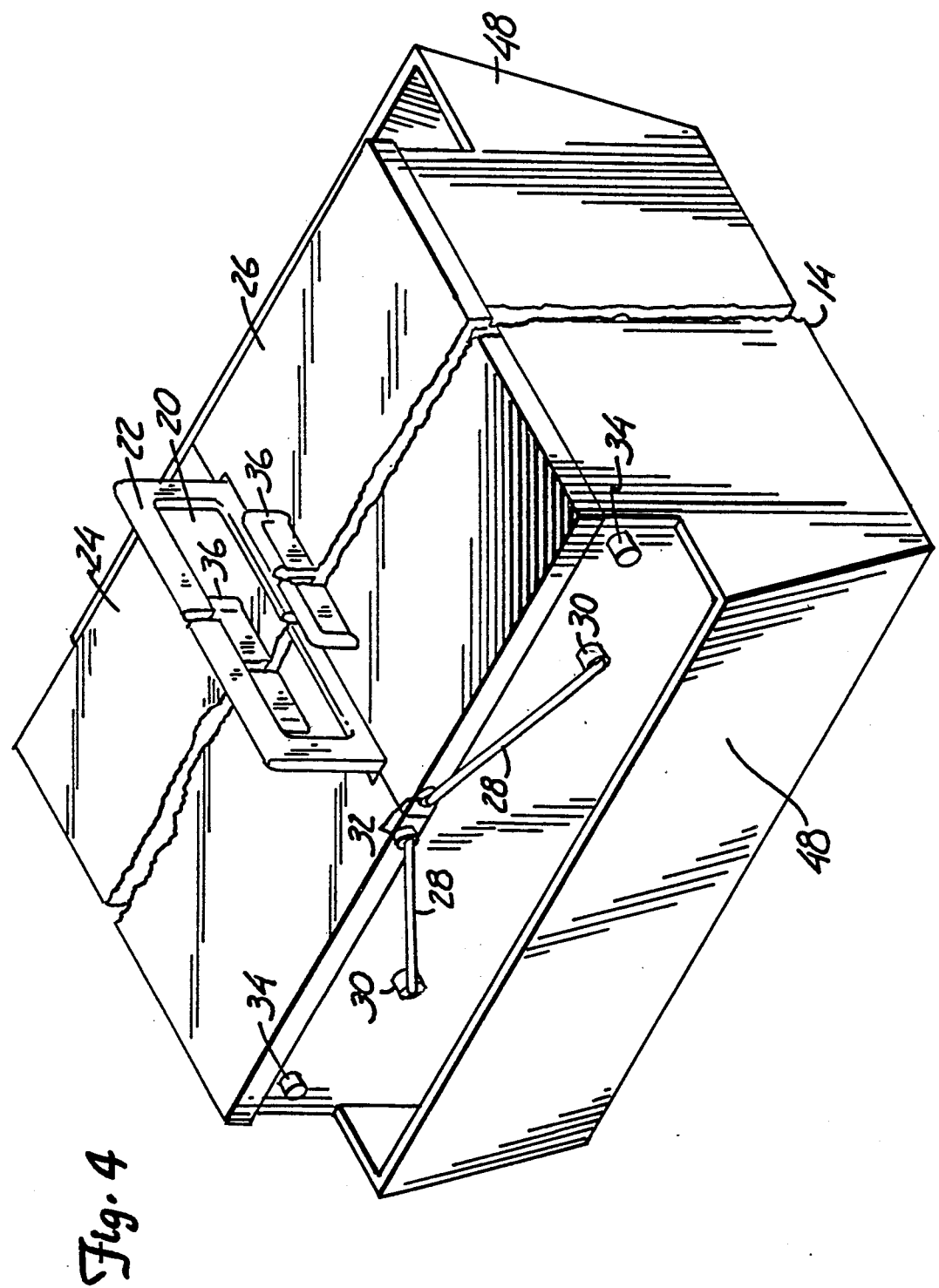
FIG. 4 is a perspective view similar to FIG. 1 illustrating the pockets for holding medical or laboratory gloves, or storing of documents.

In another preferred embodiment, as best illustrated in FIG. 4, a pocket or pouch 48 can be provided on at least one of the end walls 17 for holding a box of medical or laboratory gloves, or storing documents associated with the vial samples taken by the medical or laboratory technician. The pocket 48 protrudes outward from the end wall 17 beneath the pivot points 30 such that the pocket 48 does not impede or disturb the arms 28 from pivoting the cover lids 26 off the rim 24.

The side skirts of the cover 26 straddle the side walls 12 of the tray portion 12 when in the open position, as illustrated in FIG. 3. In the closed position, the cover 26 may be supported on stop blocks near the handle 22 and along the rim 24 at the outer side, near the stop rods 34.

A gasket may be provided between the cover lid 26 and the tray portion 12 and resting on the rim 24 to substantially prevent any leakage from escaping between the cover lid 26 and the tray portion 12.

Although the present invention has been described with reference to preferred embodiments, workers skilled in the art will recognize that changes may be made in form and detail without departing from the spirit and scope of the invention.

What is claimed is:

1. A biological vial transport tray comprising:
   a hollow tray portion having a base, a plurality of side walls and a plurality of end walls, the side walls and the end walls forming a rim around the tray portion;
   a center handle having a grip member, the center handle projecting from the base; and
   a pair of cover lids, each cover lid being pivotally connected to the end walls of the tray portion by an arm extending from a pivot point in the end walls to a pivot point in the cover lid.

2. The tray of claim 1 wherein the tray portion and the center handle are integrally molded to form a single piece of material.

3. The tray of claim 1 wherein the tray portion includes a stop rod, the stop rod being positioned such that the arm will rest against the stop rod when the cover lid is pivoted off the tray portion.

4. The tray of claim 1 wherein each cover lid includes a handle.

5. The tray of claim 1 and a retainer positioned within the tray portion such that the retainer rests upon the base and between the side walls.

6. The tray of claim 5 wherein the retainer comprises a block of shock absorbent material having at least one hole extending therethrough.

7. The tray of claim 1 and a plurality of fingers extending outward from at least one of the end walls whereby the fingers are adapted to securely hold a box of medical or laboratory gloves.

8. The tray of claim 1 and a pocket extending outward from at least one of the end walls whereby the pocket is adapted to hold a box of medical or laboratory gloves or store documents.

9. The tray of claim 1 wherein the cover lids are formed from a transparent material such that a medical technician or laboratory assistant can view the vials through the cover lids to determine whether any leakage or spillage had occurred before the cover lids are opened.

* * * * *